United States Patent
Dunbar et al.

[11] 3,943,176
[45] Mar. 9, 1976

[54] 2-(SULFUR-SUBSTITUTED)-3-HYDROXY-5,5-DIMETHYL-2-CYCLOHEXEN-1-ONES

[75] Inventors: Joseph E. Dunbar; Thomas J. Bohnert, both of Midland, Mich.

[73] Assignee: The Dow Chemical Company, Midland, Mich.

[22] Filed: May 3, 1974

[21] Appl. No.: 466,596

Related U.S. Application Data

[62] Division of Ser. No. 319,361, Feb. 29, 1972, Pat. No. 3,852,359.

[52] U.S. Cl............. 260/586 R; 260/590 C; 71/98; 71/103
[51] Int. Cl.²................ C07C 49/76; C07C 49/80
[58] Field of Search................ 260/586 R

[56] References Cited
OTHER PUBLICATIONS

Tomoeda et al., "Chem. Abstracts," Vol. 68, p. 49881f (1968).
Teruaki et al., Ibid, Vol. 76, p. 24741n (1972).
Oda et al., Ibid, Vol. 67, p. 54058b (1967).
Schultz et al., Ibid, Vol. 79, p. 136588m (1973).
Markley, Ibid, Vol. 79, pp. 115, 181h (1973).
Tishchenko et al., Ibid, Vol. 77, p. 164082u (1972).

*Primary Examiner*—Norman Morgenstern
*Attorney, Agent, or Firm*—Theodore Post; C. Kenneth Bjork

[57] ABSTRACT

Concerns compounds of the formula

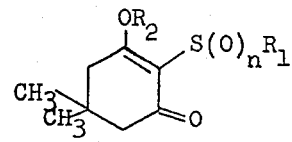

wherein $R_1$ is a 1 to 6 carbon atom alkyl, benzyl, halobenzyl, lower alkylbenzyl, nitrobenzyl, alkenyl, haloalkenyl, 2-(lower alkylthio)lower alkyl or cyclohexylmethyl group, $R_2$ is hydrogen, ammonium or alkali metal and n is an integer from 0 to 2. The compounds are prepared by reacting an alkali metal salt of 3-hydroxy-5,5-dimethyl-2-cyclohexen-1-one with a thiolsulfonate. The compounds are useful as plant growth regulators.

11 Claims, No Drawings

2-(SULFUR-SUBSTITUTED)-3-HYDROXY-5,5-DIMETHYL-2-CYCLOHEXEN-1-ONES

This is a division of application Ser. No. 319,361 Filed Dec. 29, 1972, now U.S. Pat. No. 3,852,359.

SUMMARY OF THE INVENTION

This invention concerns 2-(sulfur-substituted)-3-hydroxy-5,5-dimethyl-2-cyclohexen-1-ones corresponding to the formula

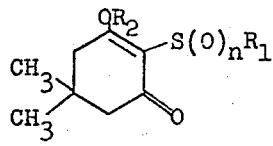

wherein $R_1$ is a 1 to 6 carbon atom alkyl, benzyl, halobenzyl, lower alkylbenzyl, nitrobenzyl, alkenyl, haloalkenyl, 2-(lower alkylthio)-lower alkyl or cyclohexylmethyl group, $R_2$ is hydrogen, ammonium or alkali metal and $n$ is an integer from 0 to 2. In the specification and claims, the term "lower alkyl" designates straight and branched chain alkyl groups having from 1 to 4 carbon atoms, the term "halo" designates fluoro, chloro or bromo, the term "alkenyl" designates an alkenyl group having from 3 to 5 carbon atoms.

The compounds are prepared by mixing together substantially equimolar proportions of an alkali metal salt of 3-hydroxy-5,5-dimethyl-2-cyclohexen-1-one with an $R_1$-thiolsulfonate according to the following equation:

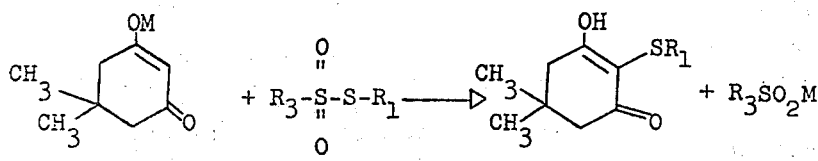

wherein M represents an alkali metal and $R_3$ represents lower alkyl, phenyl, lower alkylpehnyl, halophenyl or lower alkoxy phenyl, and, if desired, adding alkali metal or ammonium hydroxide to form the $R_2$ salt, or so forming the $R_2$ salt after subsequent oxidation of the 2-thio compound to the sulfinyl or sulfonyl compound.

The procedures for sulfenylating dimedone and preparing therefrom the corresponding sulfinyl and sulfonyl derivatives are as follows.

GENERAL PROCEDURE FOR SULFENYLATING DIMEDONE

A mixture of 3-hydroxy-5,5-dimethyl-2-cyclohexen-1-one (dimedone), and $R_1$-thiolsulfonate, an alkali metal hydroxide, water and a water-miscible solvent, i.e., methanol, ethanol, 2-propanol, acetone, methyl ethyl ketone, dimethylformamide, dioxane or acetonitrile, is heated with stirring at any temperature between about 45°C. and the boiling temperature of the aqueous solvent (preferably at the boiling temperature) for a period of time of about one hour to about 48 hours (preferably three to 24 hours). After the reaction, the solvent mixture is removed by evaporation or by distillation. The residue is washed with water to remove the sulfinate salt by-product, and the crude product is collected on a filter and dried. Purification is accomplished by recrystallizing the crude product from an organic solvent, i.e., a hydrocarbon or lower alkanol such as benzene, cyclohexane, n-hexane, methylcyclohexane, n-pentane, ethanol, aqueous ethanol, methanol, aqueous methanol or toluene or a combination thereof.

In an ultimate isolation procedure, the solvent is partially removed from the reaction mixture by evaporation or distillation, and the concentrate is cooled to cause crystallization of the product, which is then collected on a filter and recrystallized, if necessary, as shown above.

In a second alternate isolation procedure, the solvent is removed from the reaction mixture by evaporation or distillation, and the residual oil or solid is extracted with a water-immiscible organic solvent, i.e., chloroform, methylene chloride, carbon tetrachloride, 1,1,1-trichloroethane, benzene, toluene, xylene or ethyl ether, and the extract is washed with water and then extracted with 5 percent sodium hydroxide solution. The alkaline extract is washed with a water-immiscible solvent as used in the extraction and then stirred at ambient temperature with activated charcoal. The charcoal is removed by filtration, and the filtrate is acidified with a mineral acid, i.e., hydrochloric or sulfuric acid, and the precipitated solid product is collected on a filter, washed with water and dried. This product can be further pruified by recrystallization from an appropriate solvent, as shown above.

General Procedure for the Preparation of a 2-($R_1$-Sulfinyl)-3-hydroxy-5,5-dimethyl-2-cyclohexen-1-ones A mixture of the 2-($R_1$-thio)-3-hydroxy-5,5-dimethyl-2-cyclohexen-1-one, glacial acetic acid and about one, preferably, to less than two molar equivalents of hydrogen peroxide is allowed to stand at ambient temperature for about one to about 48 hours (preferably at least 20 hours). After the termination of the reaction period, the mixture is poured into ice water, and the precipitated product is collected on a filter, washed with water and dried. Further purification, if necessary, is accomplished by recrystallization from an appropriate organic solvent, i.e., n-hexane, ethanol, ethyl ether, benzene, cyclohexane or chloroform or a combination thereof.

General Procedure for the Preparation of a 2-($R_1$-sulfonyl)-3-hydroxy-5,5-dimethyl-2-cyclohexen-1-one A mixture of a 2-($R_1$-thio)-3-hydroxy-5,5-dimethyl-2-cyclohexen-1-one or 2-($R_1$-sulfinyl)-3-hydroxy-5,5-dimethyl-2-cyclohexen-1-one, glacial acetic acid and up to two molar equivalents of hydrogen peroxide (preferably two molar equivalents for the oxidation of the former reactant and one molar equivalent for the oxidation of the latter reactant) is heated at about 30° to about 100°C. (preferably at 90° to 100°C.) for a period of time of about 15 minutes to about 5 hours (preferably 1 to 1.5 hours). The mixture is then cooled and poured into ice water. The precipitated product is collected on a filter, washed with water and dried. Further purification, if necessary, is accomplished by recrystallization from an appropriate organic solvent, i.e., methanol, ethanol, 2-propanol, ethyl acetate, m-trifluoromethylbenzotrifluoride, methyl ethyl ketone, methyl isobutyl ketone or benzene.

DESCRIPTION OF SOME PREFERRED EMBODIMENTS

The following Examples illustrate the present invention and the manner and process of making and using the same but should not be construed as limitative of the overall scope of the same. Temperatures given are in Centigrade degrees. The compounds are identified by one or more of three procedures, consisting of elemental analysis, infrared and nuclear magnetic resonance (nmr) spectrometry.

EXAMPLE 1

3-Hydroxy-2-(isopropylthio)-5,5-dimethyl-2-cyclohexen-1-one

To a solution of 14.0 g. (0.100 mole) of 3-hydroxy-5,5-dimethyl-2-cyclohexen-1-one in 250 ml. of ethanol was added a solution of 4.0 g. (0.1 mole) of sodium hydroxide in 160 ml. of water followed by 23.0 g (0.100 mole) of isopropyl p-toluenethiolsulfonate. The solution was heated under reflux with stirring for seven hours and allowed to cool to room temperature. The solvent was removed by evaporation in vacuo, leaving an off-white, solid residue which was shaken and stirred thoroughly with about 250 ml. of water to remove the sulfinate salt by-product. The water-insoluble solid was collected on a filter and dried; weight 16.8 g., m.p. 74.5°–79.5°C. The crude substance was recrystallized from benzene-cyclohexane (Darco) to give an off-white, crystalline solid, m.p. 82°–83°C. A second recrystallization (methylcyclohexane) gave the pure product as off-white platelets, m.p. 83°–84°C.

Anal. Calcd. for $C_{11}H_{18}O_2S$: C, 61.64; H, 8.47; S, 14.96. Found: C, 61.35; H, 8.50; S, 14.74.

EXAMPLE 2

2-(Allylthio)-3-hydroxy-5,5-dimethyl-2-cyclohexen-1-one

A mixture of 3-hydroxy-5,5-dimethyl-2-cyclohexen-1-one (17.6 g., 0.125 mole), sodium hydroxide (5.02 g., 0.125 mole) dissolved in 100 ml. of water, allyl p-toluenethiolsulfonate (30.0 g., 0.125 mole), and 300 ml. of ethanol was heated at reflux overnight. The solvent was removed on a rotary evaporator and the remaining oil was dissolved in methylene chloride, washed with water, and then extracted with 5 percent sodium hydroxide. This basic solution was neutralized, extracted with methylene chloride, the methylene chloride solution was washed with water, dried ($Na_2SO_4$), and evaporated. The oily product was triturated with refluxing hexane and separated from the residual oil. The cooled hexane solution gave a total of 11 g. of white crystals. After recrystallization from hexane and cyclohexane the pure product had a melting point of 67.5°–69.5°C.

Anal. Calcd. for $C_{11}H_{16}O_2S$: C, 62.23; H, 7.60; S, 15.1. Found: C, 62.22; H, 7.62; S, 14.9.

EXAMPLE 3

2-[(2-Chloroallyl)thio]-3-hydroxy-5,5-dimethyl-2-cyclohexen-1-one

A mixture of 3-hydroxy-5,5-dimethyl-2-cyclohexen-1-one (25.0 g., 0.179 mole), sodium hydroxide (7.15 g., 0.179 mole) dissolved in 90 ml. of water, 2-chloroallyl p-toluenethiolsulfonate (47.0 g., 0.179 mole) and 350 ml. of ethanol was heated under reflux for 5 hours. The solvent was then partially removed and crystals formed upon cooling the solution. Filtration and three recrystallizations from EtOH/$H_2O$ gave colorless crystals (20.6 g., m.p. 103°–106°C.).

Anal. Calcd. for $C_{11}H_{15}ClO_2S$: C, 53.54; H, 6.13; Cl, 14.37; S, 12.99. Found: C, 53.43; H, 6.10; Cl, 14.53; S, 12.82.

EXAMPLE 4

3-Hydroxy-5,5-dimethyl-2-[(3-methyl-2-butenyl)-thio]-2-cyclohexen-1-one

A mixture of 3-hydroxy-5,5-dimethyl-2-cyclohexen-1-one (28.0 g., 0.200 mole), sodium hydroxide (8.0 g., 0.20 mole) dissolved in 100 ml. of water, 3-methyl-2-butenyl methanethiolsulfonate (36 g., 0.20 mole), and 400 ml. of ethanol was heated under reflux for 5.5 hours. The solvent was then removed on a rotary evaporator and the remaining oil was dissolved in methylene chloride, washed with water, and then extracted with 5 percent sodium hydroxide. This basic solution was neutralized, extracted with methylene chloride, dried ($Na_2SO_4$), and evaporated. The resulting oil was crystallized from cyclohexane to give white crystals (17.7 g., m.p. 50.5°–52°C.). An additional 6 g. of impure product (m.p. 40°–45°C.) was recovered from the mother liquor.

Anal. Calcd. for $C_{13}H_{20}O_2S$: C, 64.96; H, 8.39; S, 13.34. Found: C, 64.93; H, 8.33; S, 13.33.

EXAMPLE 5

3-Hydroxy-5,5-dimethyl-2-[(2-methylthioethyl)-thio]-2-cyclohexen-1-one

A mixture of 3-hydroxy-5,5-dimethyl-2-cyclohexen-1-one (28 g., 0.20 mole), sodium hydroxide (8.0 g., 0.20 mole) dissolved in 150 ml. of water, 2-(methylthio)ethyl methanethiolsulfonate (37.3 g., 0.200 mole), and 380 ml. of ethanol was heated under reflux for 20 hours. After removing the solvent on a rotary evaporator, the oil was dissolved in methylene chloride, washed with water, and extracted with 5 percent sodium hydroxide. This basic solution was neutralized and then extracted with methylene chloride. This methylene chloride solution was washed with saturated salt solution, dried ($Na_2SO_4$), and evaporated. The crude oil was crystallized from cyclohexane to give 17.0 g. of product. Recrystallization from cyclohexane gave white crystals as pure product, m.p. 57°–59°C.

Anal. Calcd. for $C_{11}H_{18}O_2S_2$: C, 53.62; H, 7.36; S, 26.0. Found: C, 53.7; H, 7.23; S, 26.0.

EXAMPLE 6

2-(Cyclohexylmethylthio)-3-hydroxy-5,5-dimethyl-2-cyclohexen-1-one

A mixture of 3-hydroxy-5,5-dimethyl-2-cyclohexen-1-one (28.0 g., 0.200 mole), sodium hydroxide (8.0 g., 0.20 mole) dissolved in 100 ml. of water, cyclohexylmethyl p-toluenethiolsulfonate (56.8 g., 0.200 mole) and 350 ml. of ethanol was heated under reflux for 6 hours. After removing the solvent on a rotary evaporator, the oil was dissolved in methylene chloride, washed with water, and extracted with 5 percent sodium hydroxide. This basic solution was neutralized and extracted with methylene chloride. The organic solution was washed with saturated salt solution, dried ($Na_2SO_4$), and evaporated. The oily product was crystallized from methylcyclohexane (41 g., m.p. 64°–67°C.). Further recrystallization gave white crystals, m.p. 67.5°–69.5°C.

EXAMPLE 15

2-(p-Fluorobenzylthio)-3-hydroxy-5,5-dimethyl-2-cyclohexen-1-one

A mixture of 3-hydroxy-5,5-dimethyl-2-cyclohexen-1-one (21 g., 0.15 mole), sodium hydroxide (6.0 g., 0.15 mole) dissolved in 75 ml. water, p-fluorobenzyl p-toluenethiolsulfonate (44.4 g., 0.150 mole), and 300 ml. of ethanol was heated under reflux for 3.5 hours. Removal of 150 ml. of the solvent by distillation and cooling the solution gave crystals (31.4 g., m.p. 112°–+°C.). Recrystallization from ethanol gave pure product as white crystals, m.p. 119°–121°C.

Anal. Calcd. for $C_{15}H_{17}FO_2S$: C, 64.26; H, 6.11; F, 6.78; O, 11.41; S, 11.44. Found: C,64.28; H, 6.08; F, 6.73; S, 11.45.

EXAMPLE 16

2-(p-Fluorobenzylsulfinyl)-3-hydroxy-5,5-dimethyl-2-cyclohexen-1-one

A mixture of 2-(p-fluorobenzylthio)-3-hydroxy-5,5-dimethyl-2-cyclohexen-1-one (12.4 g., 0.0443 mole) 30 percent hydrogen peroxide (5.0 g., 0.044 mole) and 100 ml. of glacial acetic acid was allowed to stand at room temperature for 24 hours. The solution was poured into ice water and the precipitated pink crystals were filtered and dried (12.3 g., m.p. 122°–125°C.).

Anal. Calcd. for $C_{15}H_{17}FO_3S$: C, 60.79; H, 5.78; F, 6.41; S, 10.82. Found: C, 60.60; H, 5.72; F, 6.1; S, 10.81.

EXAMPLE 17

3-Hydroxy-5,5-dimethyl-2-(p-nitrobenzylthio)-2-cyclohexen-1-one

A mixture of the sodium salt of 3-hydroxy-5,5-dimethyl-2-cyclohexen-1-one (17.1 g., 0.105 mole), p-nitrobenzyl methanethiolsulfonate (26 g., 0.10 mole) 200 ml. of ethanol, and 30 ml. of water was heated under reflux for 3.5 hours. Approximately 100 ml. of solvent was removed by distillation and, upon cooling crystallization occurred. After filtration and drying the solid was recrystallized from methanol to give two different crystalline forms that were manually separated. The light yellow rods were recrystallized from 2-propanol to give pure product (2.5 g., m.p. 140°–141.5°C).

Anal. Calcd. for $C_{15}H_{17}NO_4S$: C, 58.61; H, 5.58; N, 4.55; S, 10.43. Found: C,58.79; H, 5.70; N, 4.56; S, 10.49.

EXAMPLE 18

3-Hydroxy-5,5-dimethyl-2-(p-methylbenzylthio)-2-cyclohexen-1-one

A mixture of 3-hydroxy-5,5-dimethyl-2-cyclohexen-1-one (28.0 g., 0.20 mole), sodium hydroxide (8.0 g., 0.20 mole) dissolved in 100 ml. of water, p-methylbenzyl p-toluenethiolsulfonate (57.6 g., 0.200 mole) and 400 ml. of ethanol was heated at reflux for 4.75 hours. Approximately 300 ml. of solvent was removed by distillation, and upon cooling crystallization occurred. Filtration and recrystallization from ethanol gave pure product as white crystals (23 g., m.p. 100.5°–102.5°C.).

Anal. Calcd. for $C_{16}H_{20}O_2S$: C, 69.52; H, 7.29; S, 11.60. Found: C, 69.44; H, 7.25; S, 11.61.

EXAMPLE 19

3-Hydroxy-5,5-dimethyl-2-(p-methylbenzylsulfinyl)-2-cyclohexen-1-one

A mixture of 3-hydroxy-5,5-dimethyl-2-(p-methylbenzylthio)-2-cyclohexen-1-one (10 g., 0.036 mole), 30 percent hydrogen peroxide (4.11 g., 0.0362 mole), and 100 ml. of glacial acetic acid was allowed to stand at room temperature for 24 hours. The solution was poured into ice water, and the resulting pink solid was filtered and dried to give pure product (9.9 g., m.p. 89°–90.5°C.).

Anal. Calcd. for $C_{16}H_{20}O_3S$: C, 65.72; H, 6.85; S, 10.96. Found: C, 65.85; H, 6.82; S, 11.05.

EXAMPLE 20

2-Benzylthio-3-hydroxy-2,2-dimethyl-2-cyclohexen-1-one

To a solution of 28.0 g. (0.200 mole) of 3-hydroxy-5,5-dimethyl-2-cyclohexen-1-one in 500 ml. of ethanol was added a solution of 8.0 g. (0.20 mole) of sodium hydroxide in 320 ml. of water followed by 55.7 g. (0.200 mole) of benzyl p-toluenethiolsulfonate. The mixture was heated under reflux with stirring for seven hours. The solvent was removed by evaporation in vacuo, and the white, solid residue was shaken and stirred with water, collected on a filter and air dried; 50.8 g., m.p. 84°–90°C. Recrystallization from ethanol gave 33.9 g. of white crystals, m.p. 87.5°–90.5°C. Two further recrystallizations, one from aqueous ethanol and one from 2-propanol gave the pure product as white crystals, m.p. 91.5°–93°C.

Anal. Calcd. for $C_{15}H_{18}O_2S$: C, 68.67; H, 6.92; S, 12.22. Found: C, 68.35; H, 6.85; S, 12.11.

EXAMPLE 21

2-Benzylsulfinyl-3-hydroxy-5,5-dimethyl-2-cyclohexen-1-one

A solution of 10.3 g. (0.0391 mole) of 2-benzylthio-3-hydroxy-5,5-dimethyl-2-cyclohexen-1-one and 4.43 g. (0.0391 mole) of 30 percent hydrogen peroxide in 50 ml. of glacial acetic acid was allowed to stand at room temperature for 22 hours and was then poured into ice water and the mixture extracted with methylene chloride. The extract was dried over anhydrous sodium sulfate, filtered and the solvent removed by evaporation in vacuo, leaving 9.2 g. of amber viscous oil. After some difficulty in inducing crystallization, seed crystals were obtained by an ether solution of a small portion of the oil in a Dry Ice methylene chloride bath. The seed crystals, thus obtained, were used to induce crystallization of the main portion of the oil from ether-hexane to give 7.8 g. of light-pink crystals, m.p. 82°–83°C. A second recrystallization from ether-hexane gave the pure substance as light pink crystals, m.p. 82.5°–83.5°C.

Anal. Calcd. for $C_{15}H_{18}O_3S$: C, 64.72; H, 6.52; S, 11.52. Found: C, 64.91; H, 6.56; S, 11.36.

EXAMPLE 22

2-Benzylsulfonyl-3-hydroxy-5,5-dimethyl-2-cyclohexen-1-one

A solution of 12.4 g. (0.110 mole) of 30 percent hydrogen peroxide and 8.00 g. (0.0305 mole) of 2-benzylthio-3-hydroxy-5,5-dimethyl-2-cyclohexen-1-one in 65 ml. of glacial acetic acid was allowed to stand at room temperature for 1 hour and was then heated on the steam plate at 90°C. for an additional hour. The solution was cooled and poured into ice water. The resulting light tan, solid precipitate was collected on a filter and air dried; 7.7 g., m.p. 87°–89°C. Recrystallization from ethanol gave pale pink crystals, m.p.

Anal. Calcd. for $C_{15}H_{24}O_2S$: C, 67.1; H, 9.01; S, 11.9. Found: C, 67.1; H, 8.83; S, 12.0.

EXAMPLE 7

2-(Cyclohexylmethylsulfinyl)-3-hydroxy-5,5-dimethyl-2-cyclohexen-1-one

A mixture of 2-(cyclohexylmethylthio)-3-hydroxy-5,5-dimethyl-2-cyclohexen-1-one (8.0 g., 0.029 mole), 50 ml. of glacial acetic acid and 30 percent hydrogen peroxide (3.26 g., 0.029 mole) was allowed to stand at room temperature for 24 hours. The solution was then poured into ice-water, and the precipitated pink crystals were filtered and dried (7.7 g., m.p. 77°–79.5°C.).

Anal. Calcd. for $C_{15}H_{24}O_3S$: C, 63.34; H, 8.50; S, 11.27. Found: C, 63.25; H, 8.28; S, 11.11.

EXAMPLE 8

3-Hydroxy-2-isobutylthio-5,5-dimethyl-2-cyclohexen-1-one A mixture of 3-hydroxy-5,5-dimethyl-2-cyclohexen-1-one (28.0 g., 0.200 mole), sodium hydroxide (8.0 g., 0.20 mole) dissolved in 100 ml. of water, isobutyl p-toluenethiolsulfonate (48.8 g., 0.200 mole), and 350 ml. of ethanol was heated under reflux for 4.5 hours. After removing the solvent on a rotary evaporator, the oil was dissolved in methylene chloride, washed with $H_2O$, and extracted with 5 percent hydroxide. The basic aqueous solution was neutralized and extracted with methylene chloride. The methylene chloride solution was washed with saturated salt solution, dried ($Na_2SO_4$), and evaporated. The oily product was crystallized from methylcyclohexane (27.2 g., m.p. 65°–68°C.). Recrystallization from hexane gave pure product as white crystals m.p. 66°–69°C.

Anal. Calcd. for $C_{12}H_{20}O_2S$: C, 63.12; H, 8.83; S, 14.0. Found: C, 63.08; H, 8.81; S, 13.86.

EXAMPLE 9

3-Hydroxy-2-isobutylsulfinyl-5,5-dimethyl-2-cyclohexen-1-one

A mixture of 3-hydroxy-2-isobutylthio-5,5-dimethyl-2-cyclohexen-1-one (10 g., 0.044 mole), 30 percent hydrogen peroxide (5.0 g., 0.044 mole), and 100 ml. of glacial acetic acid was allowed to stand at room temperature for 19 hours. The solution was poured into ice-water and the solid filtered to give 4.7 g. of crude product. After two from hexane the pure product was obtained as pink crystals 3.3 g., m.p. b 48.5°–50°C.

Anal. Calcd. for $C_{12}H_{20}O_3S$: C, 58.98; H, 8.25; S, 13.12. Found: C, 58.75; H, 8.29; S, 12.83.

EXAMPLE 10

3-Hydroxy-2-isopentylthio-5,5-dimethyl-2-cyclohexen-1-one

A mixture of 3-hydroxy-5,5-dimethyl-2-cyclohexen-1-one (28.0 g., 0.200 mole), sodium hydroxide (8.0 g., 0.20 mole) dissolved in 100 ml. of water, isopentyl p-toluenethiolsulfonate (51.6 g., 0.200 mole), and 400 ml. of ethanol was heated under reflux for 5 hours. After removal of the solvent on a rotary evaporator, the oil was dissolved in methylene chloride, washed with water, and extracted with 5 percent sodium hydroxide. This basic solution was neutralized and then extracted with methylene chloride. The organic solution was washed with saturated salt solution, dried ($Na_2SO_4$), and evaporated. The product was crystallized from hexane (34.9 g., m.p. 55°–60°C.). Recrystallization from hexane gave the pure product as white crystals (31.2 g., 0.129 mole, 65 percent, m.p. 59°–61°C.).

Anal. Calcd. for $C_{13}H_{22}O_2S$: C, 64.42; H, 9.15; O, 13.2; S, 13.23. Found: C, 64.45; H, 9.07; S, 12.95.

EXAMPLE 11

3-Hydroxy-2-isopentylsulfinyl-5,5-dimethyl-2-cyclohexen-1-one

A mixture of 3-hydroxy-2-isopentylthio-5,5-dimethyl-2-cyclohexen-1-one (10 g., 0.041 mole), 30 percent hydrogen peroxide (4.7 g., 0.041 mole), and 100 ml. of glacial acetic acid was allowed to stand at room temperature for 24 hours. The mixture was poured into ice water and the precipitated pink crystals were filtered and dried (9.1 g., m.p. 64.5°–66°C.).

Anal. Calcd. for $C_{13}H_{22}O_3S$: C, 60.43; H, 8.58; O, 18.58; S, 12.41. Found: C, 60.50; H, 8.49; S, 12.49.

EXAMPLE 12

2-(p-Chlorobenzylthio)-3-hydroxy-5,5-dimethyl-2-cyclohexen-1one

A mixture of 3-hydroxy-5,5-dimethyl-2-cyclohexen-1-one (28.0 g., 0.200 mole), sodium hydroxide (8.0 g., 0.20 mole) dissolved in 100 ml. of water, p-chlorobenzyl p-toluenethiolsulfonate (62.6 g., 0.200 mole) and 400 ml. of ethanol was heated under reflux for four hours. Approximately 200 ml. of solvent was removed by distillation and upon cooling crystallization occurred. Crystals were collected on a filter and recrystallized from ethanol (36 g., m.p. 142°–146°C.). Recrystallization gave the pure product as white crystals, m.p. 143.5°–146°C.).

Anal. Calcd. for $C_{15}H_{17}ClO_2S$: C, 60.70; H, 5.77; Cl, 11.95; S, 10.80. Found: C, 60.51; H, 5.76; Cl, 11.96; S, 10.64.

EXAMPLE 13

2-(p-Chlorobenzylsulfinyl)-3-hydroxy-5,5-dimethyl-2-cyclohexen-1-one

A mixture of 2-(p-chlorobenzylthio)-3-hydroxy-5,5-dimethyl-2-cyclohexen-1-one (10.0 g., 0.0338 mole), 30 percent hydrogen peroxide (3.83 g., 0.0338 mole), and 350 ml. of glacial acetic acid was allowed to stand at room temperature for 23 hours. The solution was poured into ice water, and the precipitated pink solid was filtered and dried (10 g., m.p. 143.5°–145°C.).

Anal. Calcd. for $C_{15}H_{17}ClO_3S$: C, 57.59; H, 5.48; Cl, 11.34; S, 10.25. Found: C, 57.68; H, 5.52; Cl, 11.09; S, 10.41.

EXAMPLE 14

2-[(p-Chlorobenzyl)sulfonyl]-3-hydroxy-5,5-dimethyl-2-cyclohexen-1-one

To a suspension of 10.9 g. (0.0367 mole) of 2-(p-chlorobenzylthio)-3-hydroxy-5,5,-dimethyl-2-cyclohexen-1-one in 90 ml. of glacial acetic acid was added 15.0 g. (0.132 mole) of 30 percent hydrogen peroxide with stirring. Stirring was continued at room temperature for one hour, after which period of time the reaction mixture was heated between 85° and 90°C. for one hour. The mixture was then cooled and poured into ice water to give 10.5 g., of a white solid, m.p. 111°–113°C., when filtered and dried. Recrystallization from ethanol give the pure product as glistening, colorless needles, m.p. 114°–114.5°C.

Anal. Calcd. for $C_{15}H_{17}ClO_4S$: C, 54.79; H, 5.21; Cl, 10.78. Found: C, 54.49; H, 5.30; Cl, 10.9.

91°–91.5°C.

Anal. Calcd. for $C_{15}H_{18}O_4S$: C, 61.20; H, 6.16; S, 10.89. Found: C, 61.14; H, 6.07; S, 10.67.

The compounds of this invention are useful as plant growth regulators for stunting the growth of grasses, including wheat and corn. Such stunting contributes to plant health and resistance to disease. It also facilitates the more efficient mechanical harvesting of crops. With tall cereals such as wheat and corn, stunting prevents lodging. This is not to suggest that all of the compounds are equally effective on the same plants or at the same concentration. The plant growth stunters are used both in the pre-emergent form, i.e., before the seeds have sprouted, or in the foliar application after plant growth has begun. For plant growth control, the compounds can be employed in an unmodified form or dispersed on a finely divided solid and employed as dusts. Such mixtures can also be dispersed in water with or without the aid of a surface-active agent and the resulting aqueous suspensions employed as sprays. In other procedures, the products can be employed as active constituents in solvent solutions, oil-in-water or water-in-oil emulsions or aqueous dispersons. The augmented compositions are adapted to be formulated as concentrates and subsequently diluted with additional liquid or solid adjuvants to produce the ultimate treating compositions. Good results are obtained when employing compositions containing from about 2 to about 25 pounds per acre of active material for pre-emergent applications and from about 1 to about $4 \times 10^3$ parts per million (ppm) of active agent for foliar application.

In the following Table, data are presented showing the activity of representative compounds, listed by example number, as plant growth stunters wherein the active agent is used in either pre-emergent or foliar application. Plant growth stunting is measured as the difference between normal or controlled growth and stunted growth, expressed as a percentage of the normal growth. Where the stunting is 100 percent, the compound obviously is a herbicide.

TABLE I

| Pre-Emergent Example | Plant Growth Stunting: Percent Reduction/Application Rate % Reduction lb./acre | Foliar Example | % Reduction ppm × 10³ |
|---|---|---|---|
| 1 | cultured rice 30/10 | 1 | sorghum 15/4 |
|  | winter wheat 20/10 | 4 | sorghum 25/4 |
|  | corn 30/10 | 9 | sorghum 60/4 |
| 2 | cotton 50/10 | 14 | crabgrass 50/4 |
|  | crabgrass 80/20 | 15 | sorghum 50/4 |
| 3 | pigweeds 100/20 | 16 | sorghum 20/4 |
| 5 | cotton 50/20 | 20 | crabgrass 30/4 |
|  | crabgrass 50/20 |  | barnyard grass 40/4 |
| 6 | cotton 50/2 |  |  |
| 7 | cotton 50/2 |  |  |
|  | crabgrass 50/20 |  |  |
| 8 | cotton 30/5 |  |  |
|  | crabgrass 60/20 |  |  |
| 9 | cotton 50/10 |  |  |
|  | crabgrass 90/20 |  |  |
| 10 | cotton 20/2 |  |  |
|  | crabgrass 30/20 |  |  |
| 11 | cotton 40/5 |  |  |
|  | crabgrass 50/20 |  |  |
| 12 | cotton 30/5 |  |  |
|  | crabgrass 30/20 |  |  |
| 13 | cotton 40/2 |  |  |
|  | crabgrass 90/20 |  |  |
| 15 | wild oats 70/20 |  |  |
| 16 | crabgrass 70/20 |  |  |
| 17 | pigweeds 100/20 |  |  |
| 18 | cotton 30/2 |  |  |
|  | crabgrass 30/20 |  |  |
| 19 | cotton 30/2 |  |  |

TABLE I-continued

| Pre-Emergent Example | Plant Growth Stunting: Percent Reduction/Application Rate % Reduction lb./acre | Foliar Example | % Reduction ppm × 10³ |
|---|---|---|---|
|  | crabgrass 50/20 |  |  |
| 20 | cotton 30/2 |  |  |
|  | corn 40/10 |  |  |
|  | winter wheat 30/10 |  |  |
| 21 | cotton 30/2 |  |  |
|  | soybeans 30/2 |  |  |
|  | winter wheat 30/5 |  |  |
| 22 | cotton 30/5 |  |  |
|  | corn 40/5 |  |  |
|  | soybeans 60/10 |  |  |

The thiolsulfonate starting materials are prepared in the following ways:

2-Chloroallyl p-toluenethiolsulfonate

A mixture of 136 g. (0.600 mole) of potassium p-toluenethiolsulfonate and 66.6 g. (0.600 mole) of 2,3-dichloropropene in 600 ml. of acetonitrile was heated under reflux with stirring for 3.7 hours. The potassium chloride by-product was removed by addition of infusorial earth with stirring followed by filtration. The solvent was removed from the filtrate by evaporation in vacuo, leaving 128 g. of the product as an orange oil, which was pure enough for preparative purposes.

3-Methyl-2-butenyl methanethiolsulfonate

A mixture of potassium methanethiosulfonate (75 g., 0.50 mole), 1-chloro-3-methyl-2-butene (52.3 g., 0.500 mole), and 400 ml. of acetonitrile was heated under reflux with stirring for 6 hours. After cooling, the salt was removed by filtration and the solvent removed on a rotary evaporator to give the oily product. (75.8 g., $n_D^{25} = 1.5214$).

CYCLOHEXYLMETHYL P-TOLUENETHIOLSULFONATE

A mixture of 56.6 g. (0.250 mole) of potassium p-toluenethiosulfonate, 44.3 g. (0.250 mole) of cyclohexylmethyl bromide and 200 ml. of acetonitrile was heated under reflux with stirring for 4.5 hours followed by filtration to remove the potassium bromide by-product. The filtrate, on cooling, yielded 18.9 g. of white crystalline solid, m.p. 216°–219°C. (dec.), which proved to be unreacted potassium p-toluenethiosulfonate and was removed by filtration. The filtrate was concentrated on the steam bath in vacuo, and the concentrate was poured into water with stirring. The crude product precipitated as a white solid and was collected on a filter and air dried, weight 48.6 g. Recrystallization from ethanol gave the pure product as white crystals, m.p. 72.5°–73.5°C.

ISOPENTYL P-TOLUENETHIOLSULFONATE

A mixture of 60.4 g. (0.400 mole) of isopentyl bromide, 90.5 g. (0.400 mole) of potassium p-toluenethiolsulfonate and 700 ml. of ethanol was heated under reflux with stirring for eight hours and then stirred at room temperature for 13 hours. The potassium bromide by-product was removed by filtration, and the solvent was removed from the filtrate by evaporation in vacuo. The residue was taken up in methylene chloride, and the methylene chloride solution was washed with water and then dried over anhydrous magnesium sulfate. The solvent was removed by evaporation in vacuo, leaving 84 g. of the product as a light brown oil, $n_D^{25} = 1.5446$.

ISOPROPYL P-TOLUENETHIOLSULFONATE

To a solution of 88.5 g. (0.800 mole) of 2-propanesulfenyl chloride in 500 ml. of methylene chloride was added portionwise 205 g. (0.800 mole) of sodium p-toluenesulfinate, maintaining the temperature at 20°C. by means of an ice bath. The reaction mixture was then stirred at room temperature for two hours, and the by-product sodium chloride was removed by filtration. The methylene chloride was removed from the filtrate by evaporation in vacuo, leaving a dark brown oil, which was dissolved in methylene chloride, washed with water and dried over anhydrous sodium sulfate. After removal of the drying agent by filtration, the solution was treated with decolorizing charcoal, filtered and evaporated to dryness in vacuo, leaving 143 g. of the crude product. Fractionation gave the pure product as a pale yellow liquid, $n_D^{25} = 1.5540$.

P-CHLOROBENZYL P-TOLUENETHIOLSULFONATE

A mixture of 48.4 g. (0.300 mole) of p-chloro benzyl chloride, 68.0 g. (0.300 mole) of potassium p-toluenethiolsulfonate and 1200 ml. of ethanol was heated under reflux with stirring for 4.5 hours. The mixture was then further stirred at room temperature for 15 hours. The by-product potassium chloride was removed by filtration, and the ethanol was removed from the filtrate by evaporation in vacuo. The residue was shaken with water and extracted with methylene chloride. The extract was dried over anhydrous sodium sulfate, filtered and the methylene chloride removed by evaporation in vacuo, leaving the pure product as 75 g. of light yellow liquid, $n_D^{25} = 1.6059$.

P-FLUOROBENZYL P-TOLUENETHIOLSULFONATE

A mixture of potassium p-toluenethiosulfonate (56.6 g., 0.250 mole), p-fluorobenzyl chloride (36.1 g., 0.250 mole), and 400 ml. of acetonitrile was heated under reflux for 3 hours with stirring and then allowed to cool. The potassium chloride was removed by filtration, and the solvent was removed on the rotary evaporator to give the desired product as light brown oil (70.9 g., $n_D^{25} = 1.5908$).

N-NITROBENZYL METHANETHIOLSULFONATE

A mixture of 45.1 g. (0.300 mole) of potassium methanethiosulfonate and 64.8 g. (0.300 mole) of p-nitrobenzyl bromide in 400 ml. of acetonitrile was heated under reflux with stirring for 5 hours. The potassium bromide by-product was removed by filtration, and the solvent was removed from the filtrate by evaporation in vacuo, leaving a viscous oil which crystallized. Recrystallization from ethanol gave 62 g. of glistening, straw colored needles, m.p. 83°–83.5°C. A small portion was again recrystallized from ethanol to give the pure substance of the same appearance, m.p. 83.5°–84°C.

P-METHYLBENZYL-P-TOLUENETHIOLSULFONATE

A mixture of 70.5 g. (0.500 mole) of α-chloro-p-xylene and 113 g. (0.500 mole) of potassium p-toluene thiosulfonate in 1 l of ethanol was heated under reflux with stirring for 4 hours and was then stirred at room temperature for 15 hours. The reaction mixture was filtered to remove the by-product potassium chloride, and the ethanol was removed from the filtrate by evaporation in vacuo, leaving a semi-solid residue which was shaken with water and extracted with methylene chloride. The methylene chloride extract was dried over anhydrous sodium sulfate and evaporated to dryness in vacuo. The residue was crystallized (hexane) to give 116 g. of white crystals, m.p. 52°–56°C. A second recrystallization gave the pure product as white crystals, m.p. 54°–55°C.

What is claimed is:

1. A 2-(sulfur-substituted)-3-hydroxy-5,5-dimethyl-2-cyclohexen-1-one corresponding to the formula

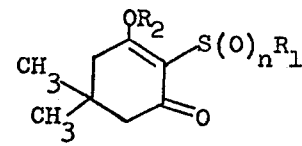

wherein $R_1$ is selected from the group consisting of alkyl of 1 to 6 carbon atoms, alkenyl and halo-alkenyl of 3-5 carbon atoms, 2-(lower alkylthio)lower alkyl and cyclohexylmethyl, $R_2$ represents hydrogen, ammonium or alkali metal and $n$ represents an integer from 0 to 2.

2. The compound of claim 1 which is 3-hydroxy-2-(isopropylthio)-5,5-dimethyl-2-cyclohexen-1-one.

3. The compound of claim 1 which is 2-(allylthio)-3-hydroxy-5,5-dimethyl-2-cyclohexen-1-one.

4. The compound of claim 1 which is 3-hydroxy-5,5-dimethyl-2-[(3-methyl-2butenyl)thio]-2-cyclohexen-1-one.

5. The compound of claim 1 which is 3-hydroxy-5,5-dimethyl-2-[(2-methylthioethyl)thio]-2-cyclohexen-1-one.

6. The compound of claim 1 which is 2-(cyclohexylmethylthio)-3-hydroxy-5,5-dimethyl-2-cyclohexen-1-one.

7. The compound of claim 1 which is 2-(cyclohexylmethylsulfinyl)-3-hydroxy-5,5-dimethyl-2-cyclohexen-1-one.

8. The compound of claim 1 which is 3-hydroxy-2-isobutylthio-5,5-dimethyl-2-cyclohexen-1-one.

9. The compound of claim 1 which is 3-hydroxy-2-isobutylsulfinyl-5,5-dimethyl-2-cyclohexen-1-one.

10. The compound of claim 1 which is 3-hydroxy-2-isopentylthio-5,5-dimethyl-2-cyclohexen-1-one.

11. The compound of claim 1 which is 3-hydroxy-2-isopentylsulfinyl-5,5-dimethyl-2-cyclohexen-1-one.

* * * * *

UNITED STATES PATENT AND TRADEMARK OFFICE
CERTIFICATE OF CORRECTION

PATENT NO. : 3,943,176
DATED : March 9, 1976
INVENTOR(S) : Joseph E. Dunbar, Thomas J. Bohnert It is certified that error appears in the above-identified patent and that said Letters Patent are hereby corrected as shown below:

Page 1 under, Related U.S. Application Data, delete "Feb" insert --Dec--.

Col. 1, line 41, delete "alkylpehnyl," insert --alkylphenyl--.

Col. 3, line 19, delete "0.1", insert --0.10--.

Col. 5, line 19, start a new paragraph after en-1-one.

Col. 5, line 26, insert after percent --sodium--.

Col. 5, line 46, insert after two --recrystallizations--.

Col. 5, line 47, delete the letter "b".

Col. 6, line 65, delete the word "give" insert --gave--.

UNITED STATES PATENT AND TRADEMARK OFFICE
CERTIFICATE OF CORRECTION

PATENT NO. : 3,943,176
DATED : March 9, 1976
INVENTOR(S) : Joseph E. Dunbar, Thomas J. Bohnert It is certified that error appears in the above-identified patent and that said Letters Patent are hereby corrected as shown below:

Col. 7, line 12, delete "+", insert --117°--.

Col. 9, line 23, delete "dispersons", insert --dispersions--.

Col. 11, line 25, delete "p-chloro benzyl", insert --p-chloro-benzyl--.

Col. 12, line 43, insert after the second 2 -- - --.

Signed and Sealed this

Nineteenth Day of October 1976

[SEAL]

Attest:

RUTH C. MASON
Attesting Officer

C. MARSHALL DANN
Commissioner of Patents and Trademarks